United States Patent [19]

Clardy et al.

[11] Patent Number: 5,476,953
[45] Date of Patent: Dec. 19, 1995

[54] BIOLOGICALLY ACTIVE AMIDES CONTAINING A BICYCLO MOIETY

[75] Inventors: Jon Clardy, Ithaca, N.Y.; Haiyin He, Westwood, N.J.

[73] Assignee: Cornell Research Foundation, Inc., Ithaca, N.Y.

[21] Appl. No.: 285,283

[22] Filed: Aug. 3, 1994

[51] Int. Cl.$^6$ .................................................. C07D 407/04
[52] U.S. Cl. .................................................. 549/364
[58] Field of Search .................................................. 549/364

[56] References Cited

PUBLICATIONS

Burres, N. S., et al, Cancer Research, 49, 5267–5274 (1989).
Fusetani N., et al, J. Org. Chem. 57, 3828–3832 (1992).
Perry, N. B., et al, J. Am. Chem. Soc., 110, 4850–4851 (1988).
Perry, N. B., et al, J. Org. Chem., 55, 223–227 (1990).
Sakemi, S., et al, J. Am. Chem. Soc. 110, 4851–4853 (1988).

*Primary Examiner*—Nicky Chan

[57] ABSTRACT

Cytotoxic metabolites are isolated by extraction and chromatography from a marine sponge of the same species as that deposited in the Zoological Museum of the University of Amsterdam under reg. no. ZMA POR. 10883. The isolated compounds belong to the genus of compounds having the structure:

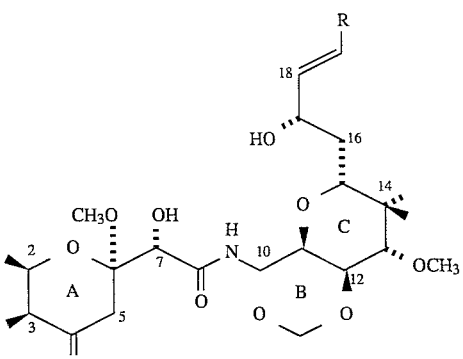

wherein R is $C_6$–$C_{12}$ alkyl or $C_6$–$C_{12}$ alkenyl having 1 or 2 double bonds, which may be interrupted with one or more imino groups and which may be substituted with one or more substituents selected from the group consisting of amino, carboxyl, hydroxy, imino and oxo.

2 Claims, No Drawings

1

BIOLOGICALLY ACTIVE AMIDES CONTAINING A BICYCLO MOIETY

The invention was made at least in part with Government support under National Institutes of Health grant number CA 50750. The Government has certain rights in the invention.

TECHNICAL FIELD

The invention is directed to a novel genus of biologically active compounds which contain a moiety the same up through position 17 of its structure as theopederin B, mycalamide A and onnamide A, but which differs from these compounds in the moiety after position 17 of its structure.

BACKGROUND OF THE INVENTION

The multitude of plant and animal species have been recognized as a potential source of biologically active compounds. A number of compounds have been isolated from marine invertebrates, and some of these have been found to be cytotoxic and antineoplastic. In view of this, marine invertebrates are being gathered and compounds are being recovered from them and screened for biological activity.

It is an object of this invention to discover and isolate previously unknown biologically active compounds from a marine invertebrate and thereby define previously unknown biologically active chemical structure.

SUMMARY OF THE INVENTION

The invention herein provides substantially pure compound having the structural formula:

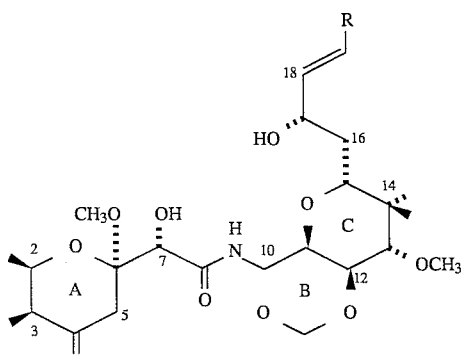

wherein R is $C_6$–$C_{12}$ alkyl or $C_6$–$C_{12}$ alkenyl having 1 or 2 double bonds, which may be interrupted with one or more imino groups and which may be substituted with one or more substituents selected from the group consisting of amino, carboxyl, hydroxy, imino and oxo. These compounds have antiviral, antitumor and immune system stimulatory function.

Compounds are known which have the same core structure as the above structure, i.e., which contain a moiety the same up through position 15 of the structure set forth above. These compounds are known as theopederin A-E, mycalamide A-B and onnamide A and are described in Burres, N. S., et al, Cancer Research, 49, 5267–5274 (1989); Fusetani, N., et al, J. Org. Chem. 57, 3828–3832 (1992); Perry, N. B., et al, J. Am. Chem. Soc., 110, 4850–4851 (1988); Perry, N. B., et al, J. Org. Chem. 55, 223–227 (1990); and Sekemi, S., et al, J. Am. Che. Soc. 110, 4851–4853 (1988). Of these compounds, theopederin B, mycalamide A and onnamide A have a moiety the same as the compounds herein up through position 17 of the structure set forth above.

The genus herein differs from the known compounds in having a double bond between the position 18 and position 19 carbons.

The term "substantially pure" is used herein to mean greater than 99% pure on a solvent free basis.

DETAILED DESCRIPTION

Two compounds within the above-described genus are metabolites of a particular marine sponge and are recoverable therefrom as described below.

The sponge specimens that constitute the source of the two compounds were collected by hand by scuba techniques in 1992 and 1993 from encrustations on coral reef walls at depths of 30 to 80 feet off the southwest side of Icadambanuan Island, near Palawan, Philippines. These sponges appear gray under water and are about ¼ inch thick on average and 7–8 inches in diameter on average and have one side which is fine textured and have other side which is porous with pores of about 1/16 inch in diameter spaced about ⅓ inch apart. The sponges have been identified as belong to the genus *Leiosella* by Dr. Mary Kay Harper of the Scripps Institute of Oceanography of La Jolla, Calif. In addition, Dr. R. Van Soest of the Institute for Taxomic Zoology, Zoological Museum, University of Amsterdam has indicated that the best slot for these sponges is the genus *Leiosella* and that the sponges would be considered as being of this genus primarily, because they have both primary and secondary fibers cored with spicule fragments. A voucher specimen of said sponge has been deposited at said Zoological Museum and has been assigned reg. no. ZMA POR. 10883.

One of the compounds that falls within the genus herein and which has been recovered from the above-described sponge in substantially pure form has the structural formula:

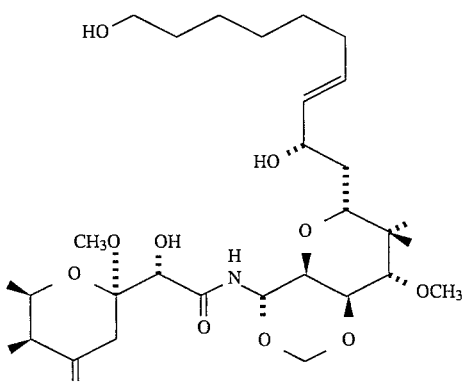

The structure of this compound has been confirmed by high resolution FABMS and IR and $^1$H and $^{13}$C NMR spectral data. The compound has been designated Icadamide B.

The second of the compounds that fall within the genus herein and which has been recovered from the above-described sponge in substantially pure form has the structural formula:

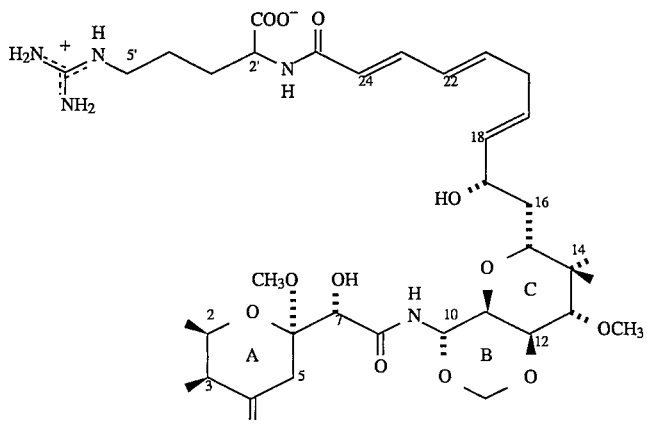

The structure of this compound has been confirmed by high resolution mass measurement and UV and IR and $^1H$ and $^{13}C$ NMR spectral data. The compound has been designated Icadamide A.

The above-described genus is set forth to embrace Icadamide A and Icadamide B as well as compounds that might be derived from Icadamide A or Icadamide B or from known compounds with the same core structure or that might be recovered from other marine sponges.

For antiviral use, the compounds herein are administered systemically to an infected animal in a substantially non-toxic antiviral effective dose.

For antitumor use, the compounds herein are administered systemically to a mammal bearing a tumor in a substantially non-toxic antitumor effective dose.

For immune system stimulation, the compounds herein are administered systemically to a mammal in need of such stimulation in a substantially non-toxic immune stimulating effective dose.

The compounds herein are intended for use parenterally or orally. They are readily distributed as dry pharmaceutical compositions containing diluents, buffers, stabilizers, solubilizers, and ingredients contributing to pharmaceutical elegance. For injection, the compounds herein are readily administered in a liposome system.

The invention is illustrated by the following examples.

EXAMPLE I

Isolation of Icadamide B and Icadamide A as Pure Compounds

Two pieces of the sponge Leiosella sp. identified by reg. no. ZMA POR. 10883, collected as described above, were utilized. These pieces each had a size of two inches by two inches by three-eighths inch.

The freshly collected sponge was frozen by placing it in a normal freezer near the collection site. It was thereafter transported frozen on dry ice to Cornell University.

Methanolic extract, obtained on thawing about 1 g frozen sponge by immersion in 20 ml methanol, was assessed for in vitro cytotoxicity in HCT116 human colon carcinoma cells using the crystal violet assay as described in Catino, J. J., et al, Cancer Chemothr. Pharmacol. 15: 240–243, 1985. Particularly, cells were plated at 4000 cells/well in 96 well microtiter plates and 24 hours later samples were added and serial diluted. The cells were incubated at 37° C. for 72 hours. The media was then removed and the cells fixed for 10 minutes with 3.7% formaldehyde in 1 X phosphate buffered saline. The fixing solution was removed and the cells stained with a 0.0075% crystal violet solution for 15 minutes. The cells were then allowed to dry. Rough IC50 values (IC50 being the drug concentration required to inhibit cell proliferation to 50% of that of untreated control cells), expressed as a dilution factor from a 2 mg/ml starting concentration, were determined by visual examination, compared to untreated control wells. The crude extract was found to be cytotoxic ($IC_{50}$=1/16384) in the bioassay.

Crude extract obtained on thawing frozen sponge (58.3 g) in 0.8 liters of methanol was evaporated under reduced pressure to provide a residue. The residue was formed into an aqueous suspension by addition of 9:1 methanol:water (about 200 ml). The aqueous suspension was triturated with ethyl acetate. The organic extract was separated by chromatography on Sephadex LH-20 using methanol as eluant and by HPLC using systems of Supelco LC-CN ($CH_3CN/H_2O$ as solvent) and Rainin-Dynamax $C_8$ ($CH_3OH/H_2O$ as solvent) successively to yield two pure compounds, Icadamide A (0.006% dry weight, based on 3.1 mg purified) and Icadamide B (0.016% dry weight, based on 9.0 mg purified). Icadamide B was isolated as a colorless oil, $[\alpha]_D$=+96° (c 0.9, MeOH) with other analytical results being as follows: IR ($AgCl_2$)3455,1690,1535 $cm^{-1}$; HRFABMS m/z 550.3387 ($MH^+$— $CH_3OH$—$H_2O$, $C_{30}H_{48}NO_8$ requires 550.3380). Icadamide A was isolated as a colorless oil, $[\alpha]_D$=+81° (c 0.12, MeOH) with other analytical results being as follows: UV (MeOH)$_{\lambda max}(\epsilon)$262(3,060)nm; IR ($AgCl_2$) 3365,1690, 1530 $cm^{-1}$; HRFABMS m/z 766 4254 ($MH^+$, $C_{37}H_{60}N_5O_{12}$ requires 766.4237).

The $^1$H and $^{13}$C NMR spectral results for Icadamide A and Icadamide B are summarized in Tables I and II below.

TABLE I $^1$H NMR Data of Compounds Icadamides A(1) and B(2) in Methanol-$d_4$.

| | Chemical Shift (multiplicity, J in Hz) | |
|---|---|---|
| $^1$H | 1 (500 MHz) | 2 (400 MHz) |
| 2 | 3.98(dq, 1.5, 6.5) | 3.88(dq, 2.4, 6.4) |
| 2-CH$_3$ | 1.18(d, 3H, 6.5) | 1.18(d, 3H, 6.4) |
| 3 | 2.19(dq, 1.5, 7) | 2.20(dq, 2.4, 7.2) |
| 3-CH$_3$ | 0.97(d, 3H, 7) | 0.97(d, 3H, 7.2) |
| 4-CH$_2$ | 4.79(br s) | 4.79(br s) |
|  | 4.64(br s) | 4.64(br s) |
| 5 | 2.42(br d, 14) | 2.42(ddd, 14.8, 2, 2) |
|  | 2.32(d, 14) | 2.32(d, 14.8) |
| 6-OCH$_3$ | 3.24(s, 3H) | 3.25(s, 3H) |
| 7 | 4.24(s) | 4.25(s) |
| 10 | 5.68(d, 9.5) | 5.68(d, 8.8) |
| 10-OCH$_3$ | 5.15(d, 6.5) | 5.15(d, 5.2) |
|  | 4.79(d, 6.5) | 4.78(d, 5.2) |
| 11 | 3.94(dd, 9.5, 6.5) | 3.96(dd, 8.8, 6.4) |
| 12 | 4.14(dd, 6.5, 6.5) | 4.15(9.2, 6.4) |
| 13 | 3.52(d, 9.5) | 3.53$^a$ |
| 13-OCH$_3$ | 3.53(s, 3H) | 3.54(s, 3H) |
| 14-CH$_3$ | 0.98(s, 3H) | 0.99(s, 3H) |
| 14-CH$_3$ | 0.85(s, 3H) | 0.85(s, 3H) |
| 15 | 3.36(br d, 8.5) | 3.35(dd, 10, 1.6) |
| 16 | 1.62(m) | 1.65(ddd, 12, 10, 8) |
|  | 1.52(ddd, 11.5. 8.5, 1.5) | 1.50(m) |
| 17 | 4.08(ddd, 8.5, 7, 5.5) | 4.03(ddd, 8, 7.6, 4.8) |
| 18 | 5.41(br dd, 15.7) | 5.32(br dd, 15.2, 7.6) |
| 19 | 5.69(ddd, 15, 8, 8) | 5.64(br ddd, 15.2, 6.8, 6.8) |
| 20 | 2.92(br dd, 2H, 8, 8) | 2.05(dt, 2H. 6.8, 6.8) |
| 21 | 6.14(ddd, 15, 7, 7) | 1.43(m, 2H) |
| 22 | 6.29(dd, 15, 11) | 1.37(m, 2H) |
| 23 | 7.14(dd, 15, 11) | 1.37(m, 2H) |
| 24 | 6.04(d, 15) | 1.54(m, 2H) |
| 25 |  | 3.54(t, 2H, 6.8) |
| 2' | 4.34(t, 6.5) |  |
| 3' | 1.88(ddt, 13, 6.5, 6.5) |  |
|  | 1.74(ddt, 13, 6.5, 6.5) |  |
| 4' | 1.62(t, 2H, 6.5) |  |
| 5' | 3.21(m, 2H) |  |

$^a$Overlapped by other signals.

TABLE II $^{13}$C NMR Data of Compounds Icadamides A(1) and B(2) in Methanol-$d_4$.

| | Chemical Shift (100 MHz) | |
|---|---|---|
| $^1$H | 1$^a$ | 2$^a$ |
| 2 | 70.9 | 70.8 |
| 2-CH$_3$ | 18.2 | 18.2 |
| 3 | 43.0 | 43.0 |
| 3-CH$_3$ | 12.4 | 12.4 |
| 4 | 148.2 | 148.2 |
| 4-CH$_2$ | 110.1 | 110.0 |
| 5 | 34.5 | 34.6 |
| 6 | 101.4 | 101.3 |
| 6-OCH$_3$ | 48.6 | 48.5 |
| 7 | 73.7 | 73.7 |
| 8 | 174.5 | 174.5 |
| 10 | 75.3 | 75.2 |
| 10-OCH$_2$ | 87.4 | 87.4 |
| 11 | 70.9 | 70.8 |
| 12 | 75.2 | 75.1 |
| 13 | 80.9 | 80.9 |
| 13-OCH$_3$ | 61.8 | 61.7 |
| 14 | b | 41.6 |
| 14-CH$_3$ | 24.0 | 23.8 |
| 14-CH$_3$ | 15.2 | 15.0 |
| 15 | 77.9 | 78.1 |
| 16 | 37.7 | 37.8 |
| 17 | 72.0 | 72.3 |
| 18 | 134.9 | 134.1 |
| 19 | 130.8$^c$ | 133.2 |
| 20 | 36.4 | 33.7 |
| 21 | 141.5 | 30.2 |
| 22 | 130.5$^c$ | 30.3 |
| 23 | 142.0 | 26.9 |
| 24 | 123.9 | 33.3 |
| 25 | 168.2 | 63.0 |
| 1' | 178.3 | |
| 2' | 55.3 | |
| 3' | 31.4 | |
| 4' | 26.1 | |
| 5' | 42.1 | |
| 7' | 158.6 | |

$^a$Assigned by analysis of a HMBC spectrum and by comparison with the assignments of onamide A.
b - Cannot be observed owing to the signal broadening and limited sample quantity.
$^c$May be interconverted.

The considerations involved for determining the structural formulas from the analytical results are set forth below.

We turn firstly to Icadamide B. The high resolution FABMS and $^1$H and $^{13}$C NMR spectral data, summarized in Tables I and II, revealed a molecular formula, $C_{31}H_{53}NO_{10}$. The $^1$H NMR spectrum indicated the presence of four carbon-attached methyls [1.18(d), 0.97 (d), 0.99 (s), and 0.85 (s)] and two hetero-atom-attached methyls [3.54(s) and 3.25(s)] in the molecule. A spin system from CH$_3$- 2(1.18), to H-2(3.88), to H-3(2.20), and to H$_3$-3(0.97) was identified by analysis of COSY spectrum. The remaining connections in ring A were identified by HMBC correlations from H-3(2.19) to C- 4(148.2) and from H-7(4.24) to C-8(174.5), C-6(101.4), and C- 5(345), together with the long-range COSY correlations from CH$_2$- 4(4.79 and 4.64) to H-5(2.42). In COSY spectrum, the spin system of H-10(5.68), H-11(3.94), H-12(4.14), and H-13(3.52) was observed. By a comparison of $^1$H and $^{13}$C NMR data of Icadamide B with those of mycalamide A and theodoperins, the core structures of these compounds from O-1 to C-16 were indicted to be identical. The side chain from C-17 to C-25 for Icadamide B was established by correlations in COSY spectrum. The chemical shift data and coupling constants of protons from H$_2$-20 to H$_2$-25 clearly indicated the presence of a primary alcohol on a free-rotating terminus and a large coupling constant (J=15.2 Hz) between H-18 and H-19 required that the H-18/H-19 double bond be in a trans geometry. The relative configurations of all the chiral centers were assigned identical to mycalamides and theopederins due to the similarity of nOe enhancement pattern of these compounds. However, the nOe between H-5 and H-17 implying a folding conformation, as was the case of theopederin A, was not observed in Icadamide B.

We turn now to Icadamide A. The molecular formula, $C_{37}H_{59}N_5O_{12}$, was determined by high resolution mass measurement. The $^1H$ and $^{13}C$ NMR spectral data of the lower part of the molecule from O-1 to C-19 were very close to the corresponding signals for Icadamide B (see Tables I and II). The signals 6178.3(s), 168.2(s), and 158.6(s) in $^{13}C$ NMR spectrum implied that there were two additional carbonyls and a guanidinium group in Icadamide A. The spin systems from $H_2$-20 to H-24, and from H'-2 to $H_2$-5' were indicated by COSY spectrum. the large coupling constants between H-21 and H-22 and between H-23 and H-24 indicated that both H-21/H-22 and H-23/H-24 double bonds have trans geometry. Finally, by requirement of molecular formula and chemical shift data, an arginine unit had to be connected to C-25 carbonyl, similar to the previously reported onnamide.

The analytical data are consistent with the structural formulas set forth above for Icadamide B and Icadamide A.

EXAMPLE II

In Vitro Cytotoxicity Testing

Cytotoxicity was assessed for pure Icadamide A and for pure Icadamide B in an HCT116 human colon carcinoma cell line by the crystal violet assay described previously. Icadamide A demonstrated an $IC_{50}$ value of 63 nM. Icadamide B demonstrated an $IC_{50}$ value of 0.17 nM. The $IC_{50}$ is the drug concentration required to inhibit cell proliferation to 50% of that of untreated control cells.

EXAMPLE III

In Vivo Antitumor Testing

For evaluation of antitumor activity against P388 mouse leukemia cells, 1 X $10^6$ P 388 leukemia cells were implanted in the intraperitoneal (ip) cavity of (BALB/c X DBA/2)$F_1$(CDF$_1$) or (C57BL/6 X DBA/2)$F_1$(BDF$_1$) mice according to the procedure as described in Rose, W. C., et al, Cancer Res. 43: 1504–1510 (1983). Icadamide B was dissolved in DMSO and diluted with saline to the desired concentrations. Injection of Icadamide B was by the ip route beginning on the first day after tumor implantation and consecutively every day for five treatments (q1dX5:1). Increases in lifespan were reflected by the median survival time of treated (T) versus control (C) groups for which a % T/C was calculated. A % T/C of ≧125% was considered an active result.

For evaluation of antitumor activity versus M109 mouse lung tumors, experiments were begun by implanting 0.5 ml of a 2.0% brei ip or 0.1 ml subcutaneously (sc) in CDF$_1$ mice as described in Rose, W. C., Cancer Treat. Rep. 65: 299–312 (1981). Icadamide B was administered either intraperitoneally (ip), intravenously (iv) or subcutaneously (sc) by alzet pump according to dosage amounts and schedule set forth in Table IV below. Results are expressed as % T/C, i.e., percentage of median survival time of treated (T) versus control (C) groups. A % T/C of ≧125% was considered an active result. Results are also expressed in terms of tumor growth inhibition, particularly the median times for tumors in treated (T) mice to reach a 1 g size minus the median times for control (C) mice to reach a 1 g size, denoted T-C. Tumor weights were interchangeable with tumor size on the basis of 1 $mm^3$=1 mg. The activity criterion for T-C is approximately equal to 4 days. Depending on the tumor volume doubling time for M109 tumors in control mice, this amount of delay in tumor growth is consistent with about one log of cell kill.

For evaluation of antitumor activity versus the asbestos-induced pulmonary squamous cell carcinoma (ASB), CDF$_1$ mice were implanted either intraperitoneally (ip) or subcutaneously (sc) with 0.5 ml or 0.1 ml of a 2% brei, respectively. Icadamide B was administered according to the dosage amounts, routes of administration and schedule set forth in Table III below. As indicated in Table III below, treatment was initiated on day 4 post-tumor implant and treatment was carried out for 5 consecutive days. Results were evaluated on the same basis as described above for M109 mouse lung tumors except that the activity criterion for tumor growth inhibition was a T-C of ≧6 days.

Results are set forth in Table III below.

TABLE III

| Tumor[1], site | OD or MTD[2] (mg/kg/inj) | Schedule, route | Maximum Effects | |
|---|---|---|---|---|
| | | | MST[3] % T/C | T–C (days) |
| P388, ip | a) 0.016 | qd 1–5, ip | 181 | |
| | b) 0.016 | qd 1–5, ip | 143 | |
| M109, ip | a) 0.016 | qd 1–5, ip | 163 | |
| | b) 0.008 | qd 1–5, ip | 150 | |
| M109, sc | a) 0.020 | d. 1, 4 & 7, iv | 135 | –0.3 |
| | b) 0.128 | d. 1, 3, 5, 7 & 9, iv | 97 | 0 |
| | c) 0.016 | qd 4–8, iv | 119 | 0.3 |
| | d) 0.013 | qd 4–8, ip | 109 | 2.5 |
| | e) 0.032–0.0537[4] | qd 4–10, scap[4] | 102 | 3.3 |
| ASB, ip | 0.008 | qd 4–8, ip | 121 | |
| ASB, sc | 0.032/0.128 | qd 4–8, iv | 129 | 3.0 |

[1]Murine tumor models used were as follows: P388 leukemia; Madison 109 lung carcinoma; Asbestos-induced pulmonary squamous cell carcinoma (ASB).
[2]Shown is either the optimal dose (OD), if the result was one of activity, or the maximum tolerated dose (MTD), or occasionally the highest dose tested, if no activity was observed. Each letter denotes a separate experimental result.
[3]MST % T/C = median survival time of treated vs control mice, x 100.
[4]SCAP = subcutaneously implanted Alzet pump (7-day pump). Amounts shown are daily mg/kg doses delivered The results in the above table show that Icadamide B demonstrates good activity against ip implanted P388 mouse leukemia (a maximally tolerated dose produced 43% and 81% increases in lifespan (143% T/C and 181% T/C in two separate experiments)) and against ip implanted M109 mouse lung tumor (maximally tolerated doses gave 63% and 50% increases in life span but poor activity against ip implanted asbestos-induced pulmonary squamous cell carcinoma (121% T/C)).

In evaluation in distal site mouse tumor models, sc implanted M109 or sc implanted ASB, Icadamide B provided marginal increases in lifespan (97 to 135% T/C) but negligible tumor growth delays (T-C=–0.3 to 3.3 days) versus sc implanted M109 and little distal site activity (129% T/C and T-C=3 days) versus sc implanted ASB.

Variations will be obvious to those skilled in the art. Therefore, the invention is defined by the claims.

What is claimed is:
1. A substantially pure compound which has the structural formula:
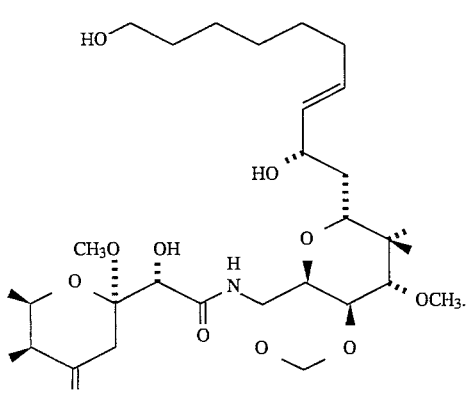
2. Substantially pure compound which has the structural formula:
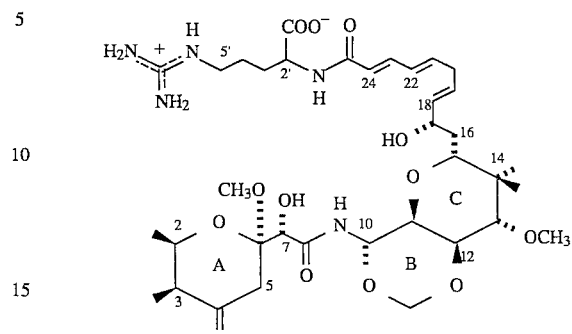
* * * * *

UNITED STATES PATENT AND TRADEMARK OFFICE
CERTIFICATE OF CORRECTION

PATENT NO. : 5,476,953  Page 1 of 2
DATED : December 19, 1995
INVENTOR(S) : Jon Clardy et al It is certified that error appears in the above-indentified patent and that said Letters Patent is hereby corrected as shown below:

In the ABSTRACT and at column 1, lines 35-50, the formula should be:

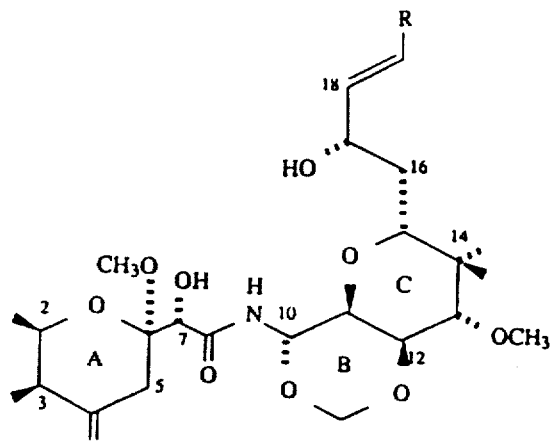

UNITED STATES PATENT AND TRADEMARK OFFICE
CERTIFICATE OF CORRECTION

PATENT NO.  : 5,476,953
DATED       : December 19, 1995
INVENTOR(S) : Jon Clardy et al It is certified that error appears in the above-indentified patent and that said Letters Patent is hereby corrected as shown below:

Claim 1 (column 9, lines 5-20), the formula should be:

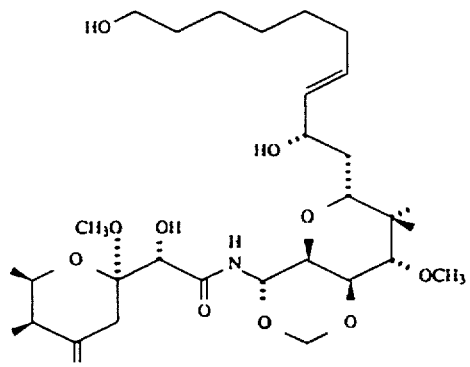

Signed and Sealed this

Twenty-seventh Day of February, 1996

Attest:

BRUCE LEHMAN

Attesting Officer           Commissioner of Patents and Trademarks